United States Patent
Yamazaki et al.

(10) Patent No.: US 9,090,502 B2
(45) Date of Patent: *Jul. 28, 2015

(54) NANOIMPRINT-MOLD RELEASE AGENT, SURFACE TREATMENT METHOD, AND NANOIMPRINT MOLD

(75) Inventors: Hiroyuki Yamazaki, Joetsu (JP); Daijitsu Harada, Joetsu (JP); Masaki Takeuchi, Joetsu (JP); Takayuki Honma, Joetsu (JP); Ayumu Kiyomori, Joetsu (JP); Tohru Kubota, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 390 days.

This patent is subject to a terminal disclaimer.

(21) Appl. No.: 13/444,138

(22) Filed: Apr. 11, 2012

(65) Prior Publication Data

US 2012/0263816 A1 Oct. 18, 2012

(30) Foreign Application Priority Data

Apr. 12, 2011 (JP) ................................. 2011-087896

(51) Int. Cl.
| | |
|---|---|
| C07F 7/04 | (2006.01) |
| B29C 59/00 | (2006.01) |
| C03C 17/30 | (2006.01) |
| B29C 37/00 | (2006.01) |
| B82Y 40/00 | (2011.01) |
| C07F 7/10 | (2006.01) |
| C07F 7/18 | (2006.01) |

(52) U.S. Cl.
CPC .............. *C03C 17/30* (2013.01); *B29C 37/0067* (2013.01); *B82Y 40/00* (2013.01); *C07F 7/10* (2013.01); *C07F 7/184* (2013.01); *C07F 7/1836* (2013.01); *C07F 7/1844* (2013.01); *C03C 2217/76* (2013.01); *C03C 2218/111* (2013.01); *C03C 2218/15* (2013.01); *C03C 2218/31* (2013.01)

(58) Field of Classification Search
CPC .................................. C07F 7/04; B29C 59/02
USPC .......................................... 556/485; 425/385
See application file for complete search history.

(56) References Cited

U.S. PATENT DOCUMENTS 5,004,824 A * 4/1991 Takaoka et al. ............... 556/412
2011/0084424 A1 4/2011 Kaida et al.

FOREIGN PATENT DOCUMENTS

| JP | 2007-73712 A | 3/2007 |
|---|---|---|
| JP | 2010-214859 A | 9/2010 |
| WO | 2009/148138 A1 | 12/2009 |

OTHER PUBLICATIONS

Ladilina, E, et al, Russian Chemical Bulletin (2009), 58(5), 1015-1022.*

* cited by examiner

*Primary Examiner* — Porfirio Nazario Gonzalez
*Assistant Examiner* — Kofi Adzamli
(74) *Attorney, Agent, or Firm* — Westerman, Hattori, Daniels & Adrian, LLP (57) ABSTRACT

A nanoimprint-mold release agent including an alkoxysilane compound represented by general formula (1) is provided

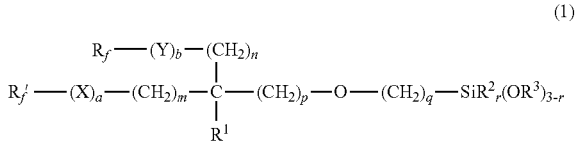

(1)

wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^2$ and $R^3$ are each independently methyl group or ethyl group; X and Y are each independently an ether linkage or an ester linkage; a and b are each 0 or 1; m, n, and p are each an integer of 0 to 6; q is an integer of 1 to 6 and r is an integer of 0 to 2.

6 Claims, 3 Drawing Sheets

NANOIMPRINT-MOLD RELEASE AGENT, SURFACE TREATMENT METHOD, AND NANOIMPRINT MOLD

CROSS-REFERENCE TO RELATED APPLICATION

This non-provisional application claims priority under 35 U.S.C. §119(a) on Patent Application No. 2011-087896 filed in Japan on Apr. 12, 2011, the entire contents of which are hereby incorporated by reference.

TECHNICAL FIELD

The present invention relates to a mold release agent used for surface treatment of a concave-convex pattern of a mold used in nanoimprint, a method of surface treating a nanoimprint mold using the same, and a nanoimprint mold obtained therefrom.

BACKGROUND ART

The nanoimprint technique is a method in which a mold with a surface having a concave-convex pattern of a nanometer size formed thereon in advance is pressed against a processing-target material or a resin coating formed on the surface thereof to precisely transfer a minute pattern all at once instead of a minute pattern formed through plural steps in a photolithography technique. The mold pattern plays a role of a so-called die and can be repeatedly used. Thus, high throughput is obtained and the cost is very low.

In transferring a minute pattern to a resin, the resin needs to be cured. The system of the nanoimprint is largely classified depending on the curing method. For example, there is known a thermal nanoimprint method of transferring a concave-convex pattern with use of a thermoplastic resin by heat and an optical nanoimprint method of transferring a concave-convex pattern with use of a photo-curable resin by light.

In particular, in the optical nanoimprint in which a resin is cured by UV light, quartz glass is generally used as a mold material. The quartz glass has been generally used in the semiconductor field. This is because of the following reason. Specifically, the quartz glass is excellent in low thermal expansion, purity, heat resistance, and chemical resistance, and therefore it easily allows achievement of high pattern accuracy. In addition, it is free from deterioration over time. Thus, it is the most suitable for the purpose of IC for which a minute pattern is necessary.

Although having excellent properties as a mold material, the quartz glass has the following problem. Specifically, the mold release performance between the quartz glass mold and a resin as the pattern-transfer-target material is low in imprint. Therefore, the resin tightly adheres to the mold when the mold is separated from the resin in which the transfer pattern is formed. Thus, an imperfection arises in the concave-convex pattern of the resin, so that a pattern defect and separation of a mold release agent are caused.

Therefore, several fluorine-based mold release agents have been attempted as a method for enhancing the mold release performance (see PCT Patent Publication No. WO 2009/148138, and JP-A 2010-214859, and JP-A 2007-073712).

SUMMARY OF THE INVENTION

Although the release effect is somewhat increased by the fluorine-based mold release agents, the problem of the pattern imperfection in mold release has not yet been completely solved. Particularly when a minute pattern is required, further higher mold release performance is necessary. Moreover, if pattern miniaturization further progresses and the pattern size becomes 10 nm order size, the influence of the thickness of the mold release agent layer on the pattern accuracy also becomes a non-ignorable level. Therefore, a compound with lower molecular weight is desired instead of a polymer resin and a long-chain compound. Furthermore, a compound having a low boiling point is preferable when mold release treatment is performed in the gas phase, and a low molecular compound is more advantageous.

SUMMARY OF THE INVENTION

The present invention has been made in consideration of the above-mentioned circumstances. Accordingly, it is an object of the present invention to provide a nanoimprint-mold release agent which is excellent in mold release performance and enables high-accuracy imprint forming, a method of surface treating a nanoimprint mold using such a mold release agent, and a nanoimprint mold obtained therefrom.

In order to attain the above object, the present inventors made extensive and intensive investigations, and, as a result, it was found that an alkoxysilane compound represented by the following general formula (1) and a silazane compound represented by the following general formula (2) are excellent in water repellency and oil repellency and provide favorable mold release performance. Furthermore, by performing surface treatment for a nanoimprint mold with these compounds, smooth mold release is achieved between the mold and a resin as the pattern-transfer-target material in imprint and the problem of the pattern imperfection can be solved. Thus, the present invention have been completed.

Therefore, the present invention provides the following nanoimprint-mold release agent, nanoimprint-mold surface treatment method, and nanoimprint mold.

[1] A nanoimprint-mold release agent comprising an alkoxysilane compound represented by the following general formula (1) or a silazane compound represented by the following general formula (2):

wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^2$ and $R^3$ are each independently methyl group or ethyl group; X and Y are each independently an ether linkage or an ester linkage; a and b are each 0 or 1; m, n, and p are each an integer of 0 to 6; q is an integer of 1 to 6 and r is an integer of 0 to 2, wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^4$ and $R^5$ are each independently an aliphatic monovalent hydrocarbon group of 1 to 6 carbon atoms in which a part or all of hydrogen atoms bonded to carbon atoms may be substituted; $R^6$ is a hydrogen atom or an aliphatic monovalent hydrocarbon group of 1 to 6 carbon atoms in which a part or all of hydrogen atoms bonded to carbon atoms may be substituted; a and b are each 0 or 1; m, n, and p are each an integer of 0 to 6; q is an integer of 1 to 6 and s is 1 or 2.

[2] The mold release agent according to [1], wherein the alkoxysilane compound of formula (1) is an alkoxysilane compound represented by the following general formula (3), (4), or (5):

(3)

wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^2$ and $R^3$ are each independently methyl group or ethyl group; X is an ether linkage or an ester linkage; q is an integer of 1 to 6 and r is an integer of 0 to 2, (4)

wherein $R_f$ and $R_f'$ are each independently a fluoroalkyl group having 1 to 10 carbon atoms; $R^1$ is a hydrogen atom or an aliphatic monovalent hydrocarbon group of 1 to 6 carbon atoms; $R^2$ and $R^3$ are each independently methyl group or ethyl group; X and Y are each independently an ether linkage or an ester linkage; q is an integer of 1 to 6 and r is an integer of 0 to 2, (5)

wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^2$ and $R^3$ are each independently methyl group or ethyl group; q is an integer of 1 to 6 and r is an integer of 0 to 2.

[3] The mold release agent according to [1], wherein the silazane compound of formula (2) is a silazane compound represented by the following general formula (10), (11), or (12):

(10)

wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^4$ and $R^5$ are each independently an aliphatic monovalent hydrocarbon group of 1 to 6 carbon atoms in which a part or all of hydrogen atoms bonded to carbon atoms may be substituted; $R^6$ is a hydrogen atom or an aliphatic monovalent hydrocarbon group of 1 to 6 carbon atoms in which a part or all of hydrogen atoms bonded to carbon atoms may be substituted; q is an integer of 1 to 6 and s is 1 or 2, (11)

wherein $R_f$ and $R_f'$ are each independently a fluoroalkyl group having 1 to 10 carbon atoms; $R^1$ is a hydrogen atom or an aliphatic monovalent hydrocarbon group of 1 to 6 carbon atoms; $R^4$ and $R^5$ are each independently an aliphatic monovalent hydrocarbon group of 1 to 6 carbon atoms in which a part or all of hydrogen atoms bonded to carbon atoms may be substituted; $R^6$ is a hydrogen atom or an aliphatic monovalent hydrocarbon group of 1 to 6 carbon atoms in which a part or all of hydrogen atoms bonded to carbon atoms may be substituted; q is an integer of 1 to 6 and s is 1 or 2, (12)

wherein $R_f$ and $R_f'$ are each independently a fluoroalkyl group having 1 to 10 carbon atoms; $R^1$ is a hydrogen atom or an aliphatic monovalent hydrocarbon group of 1 to 6 carbon atoms; $R^4$ and $R^5$ are each independently an aliphatic monovalent hydrocarbon group of 1 to 6 carbon atoms in which a part or all of hydrogen atoms bonded to carbon atoms may be substituted; $R^6$ is a hydrogen atom or an aliphatic monovalent hydrocarbon group of 1 to 6 carbon atoms in which a part or all of hydrogen atoms bonded to carbon atoms may be substituted; q is an integer of 1 to 6 and s is 1 or 2.

[4] A method of surface treating a nanoimprint-mold comprising treating the surface of the nanoimprint mold by the nanoimprint-mold release agent according to any one of claims [1] to [3].

[5] The method according to [4], wherein the surface treatment method is any of gas-phase treatment, immersion treatment, and coating treatment.

[6] A nanoimprint mold obtained by the surface treatment method according to [4] or [5].

ADVANTAGEOUS EFFECTS OF THE INVENTION

The nanoimprint-mold release agent of the present invention imparts a mold release layer with high mold release performance. Thus, it hardly gives an influence to the pattern dimension and reduces the pattern defect due to affinity in mold release. Thus, it enables high-accuracy imprint forming.

DESCRIPTION OF THE PREFERRED EMBODIMENTS

A nanoimprint-mold release agent of the present invention comprises an alkoxysilane compound represented by the following general formula (1) or a silazane compound represented by the following general formula (2):

(1)

wherein $R_f$ and $R_f'$ are each a fluoroalkyl group of 1 to 10 carbon atoms and may be identical or different from each other. $R^1$ is a hydrogen atom or an aliphatic monovalent hydrocarbon group of 1 to 6 carbon atoms. $R^2$ and $R^3$ are each methyl group or ethyl group and may be identical or different. X and Y are each an ether linkage or an ester linkage and may be identical or different. Letters a and b are each 0 or 1. Letters m, n, and p are each an integer of 0 to 6. Letter q is an integer of 1 to 6 and r is an integer of 0 to 2, (2)

wherein $R_f$ and $R_f'$ are each a fluoroalkyl group having 1 to 10 carbon atoms and may be identical or different from each other. $R^1$ is a hydrogen atom or an aliphatic monovalent hydrocarbon group of 1 to 6 carbon atoms. $R^4$ and $R^5$ are each an aliphatic monovalent hydrocarbon group of 1 to 6 carbon atoms in which a part or all of hydrogen atoms bonded to carbon atoms may be substituted, and may be identical or different. $R^6$ is a hydrogen atom or an aliphatic monovalent hydrocarbon group of 1 to 6 carbon atoms in which a part or all of hydrogen atoms bonded to carbon atoms may be substituted. Letters a and b are each 0 or 1. Letters m, n, and p are each an integer of 0 to 6. Letter q is an integer of 1 to 6 and s is 1 or 2.

Alkoxysilane Compound of Formula (1)

First, the alkoxysilane compound of formula (1) will be described.

In the general formula (1), $R_f$ and $R_f'$ are each independently a fluoroalkyl group of 1 to 10 carbon atoms. Specific examples thereof include the following linear fluoroalkyl groups: trifluoromethyl group, pentafluoroethyl group, nonafluorobutyl group, tridecafluorohexyl group, hexadecafluorooctyl group, 2,2,2-trifluoroethyl group, 3,3,3,2,2-pentafluoropropyl group, 5,5,5,4,4,3,3,2,2-nonafluoropentyl group, 7,7,7,6,6,5,5,4,4,3,3,2,2-tridecafluoroheptyl group, 9,9,9,8,8,7,7,6,6,5,5,4,4,3,3,2,2-hexadecafluorononyl group, 3,3,3-trifluoropropyl group, 4,4,4,3,3-pentafluorobutyl group, 6,6,6,5,5,4,4,3,3-nonafluorohexyl group, 8,8,8,7,7,6,6,5,5,4,4,3,3-tridecafluorooctyl group, 10,10,10,9,9,8,8,7,7,6,6,5,5,4,4,3,3-hexadecafluorodecyl group, 4,4,4-trifluorobutyl group, 5,5,5,4,4-pentafluoropentyl group, 7,7,7,6,6,5,5,4,4-nonafluoroheptyl group, 9,9,9,8,8,7,7,6,6,5,5,4,4-tridecafluorononyl group, 5,5,5-trifluoropentyl group, 6,6,6,5,5-pentafluorohexyl group, 8,8,8,7,7,6,6,5,5-nonafluorooctyl group, 10,10,10,9,9,8,8,7,7,6,6,5,5-tridecafluorodecyl group, 6,6,6-trifluorohexyl group, 7,7,7,6,6-pentafluorohexyl group, 9,9,9,8,8,7,7,6,6-nonafluorononyl group, 7,7,7-trifluoroheptyl group, 8,8,8,7,7-pentafluorooctyl group, 10,10,10,9,9,8,8,7,7-nonafluorodecyl group, 9,9,9-trifluorononyl group, and 10,10,10,9,9-pentafluorodecyl group. The specific examples further include branched fluoroalkyl groups such as 1,1,1,3,3,3-hexafluoroisopropyl group and 2,2-bis(trifluoromethyl)propyl group.

In the general formula (1), $R^1$ is a hydrogen atom or an aliphatic monovalent hydrocarbon group of 1 to 6 carbon atoms. Examples of the aliphatic monovalent hydrocarbon group of 1 to 6 carbon atoms include linear, branched, or cyclic alkyl groups and alkenyl groups. Specific examples thereof include methyl group, ethyl group, propyl group, isopropyl group, butyl group, isobutyl group, tert-butyl group, pentyl group, cyclopentyl group, hexyl group, cyclohexyl group; vinyl group, allyl group, methallyl group, and butenyl group. Preferably $R^1$ is a hydrogen atom or a methyl group.

In the above-described general formula (1), $R^2$ and $R^3$ are each independently methyl group or ethyl group.

X and Y are each an ether linkage or an ester linkage.

Letters m, n, and p are each an integer of 0 to 6, q is an integer of 1 to 6, and r is an integer of 0 to 2. Preferably, m, n, and p are each 0 or 1, q is an integer of 1 to 3, and r is 1 or 2.

Specific examples of the compounds represented by general formula (1) of the present invention include the following general formula (3) such as compounds A and B, the following general formula (4) such as compounds C to E, and the following general formula (5) such as compound F. However, the present invention is not limited thereto.

(3)

Compound A:

Compound B:

wherein $R_f$ and $R_f{}^t$ are each independently a fluoroalkyl group of 1 to 10 carbon atoms. $R^1$ is a hydrogen atom or an aliphatic monovalent hydrocarbon group of 1 to 6 carbon atoms. $R^2$ and $R^3$ are each independently methyl group or ethyl group. X is an ether linkage or an ester linkage. Letter q is an integer of 1 to 6 and r is an integer of 0 to 2.

(4)

Compound C:

Compound D:

Compound E:

wherein $R_f$ and $R_f{}^t$ are each independently a fluoroalkyl group of 1 to 10 carbon atoms. $R^1$ is a hydrogen atom or an aliphatic monovalent hydrocarbon group of 1 to 6 carbon atoms. $R^2$ and $R^3$ are each independently methyl group or ethyl group. X and Y are each independently an ether linkage or an ester linkage. Letter q is an integer of 1 to 6 and r is an integer of 0 to 2.

(5)

Compound F:

wherein $R_f$ and $R_f{}^t$ are each independently a fluoroalkyl group of 1 to 10 carbon atoms. $R^1$ is a hydrogen atom or an aliphatic monovalent hydrocarbon group of 1 to 6 carbon atoms. $R^2$ and $R^3$ are each independently methyl group or ethyl group. Letter q is an integer of 1 to 6 and r is an integer of 0 to 2.

Examples of $R_f{}^\alpha$, $R_f{}^\beta$, and $R^\gamma$ in compounds A to F include groups in the following Table 1 and Table 2. $R_f{}^\alpha$ and $R_f{}^\beta$ may be identical or different from each other.

TABLE 1

| Examples of $R_f{}^\alpha$ and $R_f{}^\beta$ in Compounds A to F |
|---|
| —$CF_3$ |
| —$(CF_2)_2F$ |
| —$(CF_2)_4F$ |
| —$(CF_2)_6F$ |
| —$(CF_2)_8F$ |
| —$CH_2CF_3$ |
| —$CH_2(CF_2)_2F$ |
| —$CH_2(CF_2)_4F$ |
| —$CH_2(CF_2)_6F$ |
| —$CH_2(CF_2)_8F$ |
| —$(CH_2)_2CF_3$ |
| —$(CH_2)_2(CF_2)_2F$ |
| —$(CH_2)_2(CF_2)_4F$ |
| —$(CH_2)_2(CF_2)_6F$ |
| —$(CH_2)_2(CF_2)_8F$ |
| —$(CH_2)_3CF_3$ |
| —$(CH_2)_3(CF_2)_2F$ |
| —$(CH_2)_3(CF_2)_4F$ |
| —$(CH_2)_3(CF_3)_6F$ |
| —$(CH_2)_4CF_3$ |
| —$(CH_2)_4(CF_2)_2F$ |
| —$(CH_2)_4(CF_2)_2F$ |
| —$(CH_2)_4(CF_2)_6F$ |
| —$(CH_2)_5CF_3$ |
| —$(CH_2)_5(CF_2)_2F$ |
| —$(CH_2)_5(CF_2)_4F$ |
| —$(CH_2)_6CF_3$ |
| —$(CH_2)_6(CF_2)_2F$ |
| —$(CH_2)_6(CF_2)_4F$ |
| —$(CH_2)_8CF_3$ |
| —$(CH_2)_8(CF_2)_2F$ |
| —$CH(CF_3)_2$ |
| —$CH_2C(CH_3)(CF_3)_2$ |

TABLE 2

| Examples of $R^\gamma$ in compounds A to F |
|---|
| —$Si(OCH_3)_3$ |
| —$Si(CH_3)(OCH_3)_2$ |
| —$Si(CH_3)_2(OCH_3)$ |
| —$Si(OC_2H_5)_3$ |
| —$Si(CH_3)(OC_2H_5)_2$ |
| —$Si(CH_3)_2(OC_2H_5)$ |

A manufacturing method of the alkoxysilane compound having two fluoroalkyl groups of formula (1) is a method of causing a reaction between olefin having two fluoroalkyl groups and represented by the following general formula (6) and a hydride alkoxysilane compound of the following general formula (7). It is preferred that the reaction be carried out under the existence of a transition metal catalyst. A platinum catalyst is preferable as the transition metal catalyst.

(6)

wherein $R_f$ and $R_f^1$ are each independently a fluoroalkyl group of 1 to 10 carbon atoms. $R^1$ is a hydrogen atom or an aliphatic monovalent hydrocarbon group of 1 to 6 carbon atoms. X and Y are each independently an ether linkage or an ester linkage. Letters a and b are each 0 or 1. Letter m is an integer of 0 to 6. Letter n is an integer of 0 to 6. Letter p is an integer of 0 to 6. Letter q' is an integer of 0 to 4.

(7)

wherein $R^2$ and $R^3$ are each independently methyl group or ethyl group. Letter r is an integer of 0 to 2.

In the above-described general formulas (6) and (7), the definitions of $R_f$, $R_f^1$, $R^1$, $R^2$, $R^3$, X, Y, m, n, p, r, a, and b are the same as those in the above-described general formula (1). Letter q' is an integer of 0 to 4 and preferably 1.

Specific examples of the compound of formula (6) include the following compounds a to f. However, the present invention is not limited thereto.

Compound a:

Compound b:

Compound c:

Compound d:

Compound e:

Compound f:

Examples of $R_f^\alpha$ and $R_f^\beta$ in compounds a to f include the groups in Table 1. $R_f^\alpha$ and $R_f^\beta$ may be identical or different.

Specific examples of the hydride alkoxysilane compounds of the general formula (7) used in the above-described reaction include trimethoxysilane, methyldimethoxysilane, dimethylmethoxysilane, triethoxysilane, methyldiethoxysilane, and dimethylethoxysilane.

The ratio between the compound of formula (6) and the hydride alkoxysilane compound of formula (7) is not particularly limited. From a viewpoint of reactivity and productivity, it is preferred that the amount of hydride alkoxysilane compound of formula (7) be in the range of 0.5 to 2 mol, particularly 0.7 to 1.2 mol per 1 mol of the compound of formula (6).

Examples of the platinum catalysts used in the reaction include chloroplatinic acid, an alcohol solution of chloroplatinic acid, a toluene or xylene solution of platinum-1,3-divinyl-1,1,3,3-tetramethyldisiloxane complex, tetrakis(triphenylphosphine)platinum, dichlorobis(triphenylphosphine)platinum, dichlorobis(acetonitrile)platinum, dichlorobis(benzonitrile)platinum, and dichloro(cyclooctadiene)platinum.

The amount of platinum catalyst is not particularly limited. From a viewpoint of reactivity and productivity, it is preferred that the amount be 0.000001 to 0.01 mol, particularly 0.00001 to 0.001 mol per 1 mol of the compound of formula (6).

The reaction temperature of the reaction is not particularly limited. However, it is preferred that the reaction temperature be 0 to 120° C., particularly 20 to 100° C., and it is preferred that the reaction time be 1 to 20 hours, particularly 1 to 10 hours.

Although the reaction proceeds without a solvent, it can use a solvent. Examples of the solvents include the following substances: hydrocarbon solvents such as pentane, hexane, cyclohexane, heptane, isooctane, benzene, toluene, and xylene; ether solvents such as diethyl ether, tetrahydrofuran, and dioxane; ester solvents such as ethyl acetate and butyl acetate; aprotic polar solvents such as acetonitrile and N,N-dimethylformamide; and chlorinated hydrocarbon solvents such as dichloromethane and chloroform. These solvents may be used alone or in combination of two or more.

Compounds a to f can be manufactured by the known methods according to the following formulas.

wherein $R_f$ and $R_f'$ are each independently a fluoroalkyl group of 1 to 10 carbon atoms. $R^1$ is a hydrogen atom or an aliphatic monovalent hydrocarbon group of 1 to 6 carbon atoms. $R^2$ is methyl group or ethyl group. X and Y are each independently an ether linkage or an ester linkage. Letter a is 0 or 1 and b is 0 or 1. Letters m, n, and p are each an integer of 0 to 6. Letter q is an integer of 1 to 6 and r is an integer of 0 to 2.

$$R^3OH \quad (9)$$

wherein $R^3$ is a methyl group or an ethyl group.

In the above-described general formulas (8) and (9), $R_f$, $R_f'$, $R^1$, $R^2$, $R^3$, X, Y, m, n, p, q, r, a, and b are the same as those in the above-described general formula (1).

Specific examples of the compounds of formula (8) of the present invention include the following compounds I to VI. However, the present invention is not limited thereto.

Compound I:

Compound II:

Compound III:

Compound IV:

Compound V:

A method of preparing the alkoxysilane compound having two fluoroalkyl groups of formula (1) is a method of causing a reaction between a chlorosilane compound having two fluoroalkyl groups of the following general formula (8) and a compound of the following general formula (9).

Compound VI:

Examples of $R_f^\alpha$ and $R_f^\beta$ in compounds I to VI include the groups in Table 1 shown above. $R_f^\alpha$ and $R_f^\beta$ may be identical or different from each other.

Examples of $R^\delta$ include —$SiCl_3$, —$Si(CH_3)Cl_2$, and —$Si(CH_3)_2Cl$.

Specific examples of the compounds of formula (9) include methanol and ethanol.

The ratio between the compound of formula (8) and the compound of formula (9) is not particularly limited. However, from a viewpoint of reactivity and productivity, it is preferred that the amount of compound of formula (9) be in the range of 0.5 to 2.0 mol, particularly 0.7 to 1.2 mol per 1 mol of Si—Cl bonding of the compound of formula (8).

In the above-described alkoxylation reaction, the reaction may be conducted under the existence of a basic compound in the reaction system in order to trap hydrogen chloride generated in the reaction. Specific examples of the basic compounds include the following substances: amine compounds such as methylamine, dimethylamine, trimethylamine, ethylamine, diethylamine, triethylamine, methyldiisopropylamine, butylamine, dibutylamine, tributylamine, 2-ethylhexylamine, ethylenediamine, pyrrolidine, N-methylpyrrolidine, piperidine, N-methylpiperidine, aniline, n-methylaniline, N,N-dimethylaniline, and toluidine; nitrogen-containing aromatic compounds such as pyridine, quinoline, isoquinoline, picoline, and lutidine; ammonia; and metal alkoxide compound such as sodium methoxide and sodium ethoxide.

It is preferred that the additive amount of the basic compound be 0.5 to 2.0 mol, particularly 0.7 to 1.2 mol per 1 mol of Si—Cl bonding of the compound of formula (8).

Although the reaction proceeds without a solvent, it is also possible to use a solvent. Examples of the solvents include the following substances: hydrocarbon solvents such as pentane, hexane, cyclohexane, heptane, isooctane, benzene, toluene, and xylene; ether solvents such as diethyl ether, tetrahydrofuran, and dioxane; ester solvents such as ethyl acetate and butyl acetate; aprotic polar solvents such as acetonitrile and N,N-dimethylformamide; and chlorinated hydrocarbon solvents such as dichloromethane and chloroform. These solvents may be used alone or in combination of two or more. The amount of solvent can be set in a normal amount range.

Although the above-described reaction condition is not particularly limited, the reaction temperature can be set to −20 to 150° C., particularly 0 to 100° C., and the reaction time can be set to 1 to 20 hours, particularly 2 to 10 hours.

It is also possible to isolate the compound of formula (1) from the hydrosilylation reaction mixture or alkoxylation reaction mixture by a purification method such as distillation or column separation. In particular, isolation by distillation is preferable because high purity can be achieved. Although there is no particular limitation on the condition of the distillation, it is preferred to perform it under reduced pressure to lower the boiling point.

Silazane Compound of Formula (2)

In the general formula (2), $R_f$ and $R_f'$ are each independently a fluoroalkyl group of 1 to 10 carbon atoms. As described above, specific examples thereof include the following linear fluoroalkyl groups: trifluoromethyl group, pentafluoroethyl group, nonafluorobutyl group, tridecafluorohexyl group, hexadecafluorooctyl group, 2,2,2-trifluoroethyl group, 3,3,3,2,2-pentafluoropropyl group, 5,5,5,4,4,3,3,2,2-nonafluoropentyl group, 7,7,7,6,6,5,5,4,4,3,3,2,2-tridecafluoroheptyl group, 9,9,9,8,8,7,7,6,6,5,5,4,4,3,3,2,2-hexadecafluorononyl group, 3,3,3-trifluoropropyl group, 4,4,4,3,3-pentafluorobutyl group, 6,6,6,5,5,4,4,3,3-nonafluorohexyl group, 8,8,8,7,7,6,6,5,5,4,4,3,3-tridecafluorooctyl group, 10,10,10,9,9,8,8,7,7,6,6,5,5,4,4,3,3-hexadecafluorodecyl group, 4,4,4-trifluorobutyl group, 5,5,5,4,4-pentafluoropentyl group, 7,7,7,6,6,5,5,4,4-nonafluoroheptyl group, 9,9,9,8,8,7,7,6,6,5,5,4,4-tridecafluorononyl group, 5,5,5-trifluoropentyl group, 6,6,6,5,5-pentafluorohexyl group, 8,8,8,7,7,6,6,5,5-nonafluorooctyl group, 10,10,10,9,9,8,8,7,7,6,6,5,5-tridecafluorodecyl group, 6,6,6-trifluorohexyl group, 7,7,7,6,6-pentafluorohexyl group, 9,9,9,8,8,7,7,6,6-nonafluorononyl group, 7,7,7-trifluoroheptyl group, 8,8,8,7,7-pentafluorooctyl group, 10,10,10,9,9,8,8,7,7-nonafluorodecyl group, 9,9,9-trifluorononyl group, and 10,10,10,9,9-pentafluorodecyl group. The specific examples further include branched fluoroalkyl groups such as 1,1,1,3,3,3-hexafluoroisopropyl group and 2,2-bis(trifluoromethyl)propyl group.

In the general formula (2), $R^1$ is a hydrogen atom or an aliphatic monovalent hydrocarbon group of 1 to 6 carbon atoms. Examples of the aliphatic monovalent hydrocarbon groups having 1 to 6 carbon atoms include linear, branched, or cyclic alkyl group and alkenyl group. As described above, specific examples thereof include methyl group, ethyl group, propyl group, isopropyl group, butyl group, isobutyl group, tert-butyl group, pentyl group, cyclopentyl group, hexyl group, cyclohexyl group, vinyl group, allyl group, methallyl group, and butenyl group. Preferably $R^1$ is a hydrogen atom or a methyl group.

In the general formula (2), $R^4$ and $R^5$ are each independently an aliphatic monovalent hydrocarbon group of 1 to 6 carbon atoms. Examples thereof include linear, branched, or cyclic alkyl group and alkenyl group. Specific examples thereof include methyl group, ethyl group, propyl group, isopropyl group, butyl group, isobutyl group, tert-butyl group, pentyl group, cyclopentyl group, hexyl group, cyclohexyl group, vinyl group, allyl group, methallyl group, and butenyl group. Preferably $R^4$ and $R^5$ are methyl group, ethyl group, or isopropyl group. Furthermore, a part or all of hydrogen atoms bonded to carbon atoms may be substituted. Specific examples of this substituent include alkoxy groups such as methoxy group, ethoxy group, and (iso)propoxy group, halogen atoms such as fluorine atom, chlorine atom, bromine atom, and iodine atom, cyano group, amino group, aryl groups having 6 to 18 carbon atoms such as phenyl group and tolyl group, aralkyl groups having 7 to 18 carbon atoms such as benzyl group and phenethyl group, ester group, ether group, acyl group, sulfide group, alkylsilyl group, and alkoxysilyl group.

In the general formula (2), $R^6$ is a hydrogen atom or an aliphatic monovalent hydrocarbon group of 1 to 6 carbon atoms. Examples of the aliphatic monovalent hydrocarbon groups include linear, branched, or cyclic alkyl group and alkenyl group. Specific examples of $R^6$ include hydrogen atom, methyl group, ethyl group, propyl group, isopropyl group, butyl group, isobutyl group, tert-butyl group, pentyl group, cyclopentyl group, hexyl group, cyclohexyl group, vinyl group, allyl group, methallyl group, and butenyl group. Preferably $R^6$ is methyl group, ethyl group, or isopropyl group. Furthermore, a part or all of hydrogen atoms bonded to carbon atoms may be substituted. Specific examples of this substituent include alkoxy groups such as methoxy group, ethoxy group, and (iso)propoxy group, halogen atoms such as fluorine atom, chlorine atom, bromine atom, and iodine atom, cyano group, amino group, aryl groups having 6 to 18 carbon atoms such as phenyl group and tolyl group, aralkyl groups having 7 to 18 carbon atoms such as benzyl group and phenethyl group, ester group, ether group, acyl group, sulfide group, alkylsilyl group, and alkoxysilyl group.

Letters m, n, and p are each an integer of 0 to 6, q is an integer of 1 to 6, and s is 1 or 2. Preferably, m, n, and p are each 0 or 1, q is an integer of 1 to 3, and s is 1 or 2.

Specific examples of the compounds of formula (2) of the present invention include the following general formula (10) such as compound G, the following general formula (11) such as compound H, and the following general formula (12) such as compound I. However, the present invention is not limited by the examples.

Compound G:

wherein $R_f$ and $R_f'$ are each independently a fluoroalkyl group of 1 to 10 carbon atoms. $R^1$ is a hydrogen atom or an aliphatic monovalent hydrocarbon group of 1 to 6 carbon atoms. $R^4$ and $R^5$ are each independently an aliphatic monovalent hydrocarbon group of 1 to 6 carbon atoms in which a part or all of hydrogen atoms bonded to carbon atoms may be substituted. $R^6$ is a hydrogen atom or an aliphatic monovalent hydrocarbon group of 1 to 6 carbon atoms in which a part or all of hydrogen atoms bonded to carbon atoms may be substituted. Letter q is an integer of 1 to 6 and s is 1 or 2.

Compound H:

wherein $R_f$ and $R_f'$ are each independently a fluoroalkyl group of 1 to 10 carbon atoms. $R^1$ is a hydrogen atom or an aliphatic monovalent hydrocarbon group of 1 to 6 carbon atoms. $R^4$ and $R^5$ are each independently an aliphatic monovalent hydrocarbon group of 1 to 6 carbon atoms in which a part or all of hydrogen atoms bonded to carbon atoms may be substituted. $R^6$ is a hydrogen atom or an aliphatic monovalent hydrocarbon group of 1 to 6 carbon atoms in which a part or all of hydrogen atoms bonded to carbon atoms may be substituted. Letter q is an integer of 1 to 6 and s is 1 or 2.

Compound I:

wherein and $R_f$ are $R_f'$ each independently a fluoroalkyl group of 1 to 10 carbon atoms. $R^1$ is a hydrogen atom or an aliphatic monovalent hydrocarbon group of 1 to 6 carbon atoms. $R^4$ and $R^5$ are each independently an aliphatic monovalent hydrocarbon group of 1 to 6 carbon atoms in which a part or all of hydrogen atoms bonded to carbon atoms may be substituted. $R^6$ is a hydrogen atom or an aliphatic monovalent hydrocarbon group of 1 to 6 carbon atoms in which a part or all of hydrogen atoms bonded to carbon atoms may be substituted. Letter q is an integer of 1 to 6 and s is 1 or 2.

Examples of $R_f^\alpha$ and $R_f^\beta$ in compounds G to I include the groups in Table 1 shown above. $R_f^\alpha$ and $R_f^\beta$ may be identical or different.

A manufacturing method of the silazane compound having two fluoroalkyl groups of the general formula (2) is a method of causing a reaction between a monochlorosilane compound having two fluoroalkyl groups of the following general formula (13) and an amine compound of the following general formula (14).

wherein $R_f$ and $R_f'$ are each independently a fluoroalkyl group of 1 to 10 carbon atoms. $R^1$ is a hydrogen atom or an aliphatic monovalent hydrocarbon group of 1 to 6 carbon atoms. $R^4$ and $R^5$ are each independently an aliphatic monovalent hydrocarbon group of 1 to 6 carbon atoms in which a part or all of hydrogen atoms bonded to carbon atoms may be substituted. Letters a and b are each 0 or 1. Letters m, n, and p are each an integer of 0 to 6. Letter q is an integer of 1 to 6.

wherein $R^6$ is a hydrogen atom or an aliphatic monovalent hydrocarbon group of 1 to 6 carbon atoms in which a part or all of hydrogen atoms bonded to carbon atoms may be substituted. Letter s is 1 or 2.

In the general formulas (13) and (14), $R_f$, $R_f'$, $R^1$, $R^2$, $R^3$, $R^4$, m, n, p, q, s, a, and b are the same as those in the above-described general formula (2).

Specific examples of the compounds of formula (13) include the following compounds g to i. However, the present invention is not limited by the examples.

Compound g:

Compound h:

Compound i:

Examples of $R_f^\alpha$ and $R_f^\beta$ in compounds g to i include the groups in Table 1 shown above. $R_f^\alpha$ and $R_f^\beta$ may be identical or different.

Specific examples of the amine compound of formula (14) used in the above-described reaction include ammonia, methylamine, ethylamine, propylamine, butylamine, dimethylamine, diethylamine, dipropylamine, and dibutylamine. Among them, ammonia, methylamine, ethylamine, dimethylamine, or diethylamine is preferred.

The ratio between the monochlorosilane compound of formula (13) and the amine compound of formula (14) is not particularly limited. However, from a viewpoint of reactivity and productivity, it is preferred that the amount of amine compound of formula (14) be in the range of 2 to 10 mol, particularly 2 to 3 mol per 1 mol of the compound of formula (13).

The above-described reaction is a dehydrochlorination reaction and it is preferred to trap the hydrochloric acid as an ammonium salt by the amine compound. Examples of the amine compounds include those compound of the general formula (14) shown above and the other known tertiary amine compounds. Examples of the tertiary amine compounds include triethylamine, amidines such as 1,8-diazabicyclo[5.4.0]-7-undecene, and nitrogen-containing aromatic compounds such as pyridine, quinoline, isoquinoline, picoline, and lutidine. The amount of the amine compound is preferably 1.0 to 2.0 mol per 1 mol of monochlorosilane. The ammonium salt formed can be removed by the known method. Examples of the method include filtration, liquid-liquid extraction, and decantation.

It is also possible to use a phase transfer catalyst in the present reaction. Examples of the phase transfer catalysts include quaternary ammonium halide compounds, quaternary phosphonium halide compounds, and crown ethers. Specific examples thereof include tetramethylammonium chloride, tetraethylammonium chloride, tetrapropylammonium chloride, tetrabutylammonium chloride, trioctylmethylammonium chloride, cetyltrimethylammonium chloride, benzyltrimethylammonium chloride, tetrabutylphosphonium chloride, tetraphenylphosphonium chloride, tetramethylammonium bromide, tetraethylammonium bromide, tetrapropylammonium bromide, tetrabutylammonium bromide, trioctylmethylammonium bromide, cetyltrimethylammonium bromide, benzyltrimethylammonium bromide, tetrabutylphosphonium bromide, tetraphenylphosphonium bromide, tetramethylammonium iodide, tetraethylammonium iodide, tetrapropylammonium iodide, tetrabutylammoniumiodide, trioctylmethylammonium iodide, cetyltrimethylammonium iodide, benzyltrimethylammonium iodide, tetrabutylphosphonium iodide, and tetraphenylphosphonium iodide.

The amount of the phase transfer catalyst is not particularly limited, and the catalytic amount can be used. From a viewpoint of reactivity and productivity, it is preferred that the amount be in the range of 0.001 to 1 mol, particularly 0.003 to 0.05 mol per 1 mol of monochlorosilane compound of formula (13). If the amount of catalyst is smaller than 0.001 mol, sufficient effects of the catalyst may not be expressed. If the amount surpasses 0.1 mol, the reaction acceleration effect may not be exerted furthermore.

Although the above-described reaction proceeds without a solvent, it can use a solvent. Examples of the solvents include the following substances: hydrocarbon solvents such as pentane, hexane, cyclohexane, heptane, isooctane, benzene, toluene, and xylene; ether solvents such as diethyl ether, tetrahydrofuran, and dioxane; ester solvents such as ethyl acetate and butyl acetate; aprotic polar solvents such as acetonitrile and N,N-dimethylformamide; and chlorinated hydrocarbon solvents such as dichloromethane and chloroform. These solvents may be used alone or a combination of two or more. The solvent can be used in a normal amount range.

Although the reaction temperature is not particularly limited, it is preferred that the reaction temperature be 0 to 120° C., particularly 0 to 70° C., and it is preferred that the reaction time be 1 to 20 hours, particularly 1 to 10 hours.

Olefin as the basic component of compounds g to i can be manufactured by the known method by the following formulas, and compounds g to i are obtained through the reaction with the corresponding hydride dialkylchlorosilane compound.

It is possible to isolate the compound of formula (2) from the reaction mixture by a purification method such as distillation or column separation. In particular, isolation by distillation is preferable because high purity can be achieved. Although there is no particular limitation on the condition of the distillation, it is preferred to perform it under reduced pressure to lower the boiling point.

Surface Treatment Method

In the surface treatment method of the present invention, the surface of the mold is treated by using the nanoimprint-mold release agent of the above-described formula (1) or (2).

As the material of the mold used in the present invention, any materials such as soda-lime glass, borosilicate glass, fused quartz glass, and synthetic quartz glass may be used. In particular, the synthetic quartz glass has a large track record in use for the semiconductor and is excellent in the properties and the accuracy.

Synthetic quartz glass prepared through the following process is preferably used as the mold. Specifically, a synthetic quartz glass ingot manufactured by causing a reaction of an organic silane compound as the starting component by oxyhydrogen flame is molded into a desired shape, followed by annealing treatment. Subsequently, after surface or cylindrical grinding, the glass is sliced to a desired thickness. Thereafter, grinding and polishing of the outer circumference according to need are conducted. Furthermore, rough polishing, fine polishing, and cleaning are conducted and the resulting glass is used.

In carrying out the specific surface treatment method of the present invention, it is preferred to perform precision cleaning of the surface of the nanoimprint mold on which a pattern is drawn in advance by a photolithography step using a photoresist material. Contamination of the glass surface would preclude successful mold release treatment and also cause a defect of the imprint.

When the mold is surface treated, immersion treatment, spin-coating, spray-coating, or gas-phase treatment method can be employed. Among them, gas-phase treatment is particularly preferable in view of prevention of contamination and adherence of an excess substance. In the case of the gas-phase treatment, an undiluted solution of the mold release agent or a diluted solution thereof by a solvent is evaporated at an ordinary temperature or by heating and the vapor is brought into contact and reacted with the mold. Besides the heating, the evaporation by bubbling of a dry nitrogen gas is effectively assisted.

It is also effective to conduct the reaction with heating of the mold in the gas-phase treatment in view of reaction acceleration. Although there is no limitation on the heating temperature of the mold, it is preferred that the temperature be 5.0 to 150° C., particularly 70 to 90° C. Furthermore, heat treatment may be further conducted after the gas-phase treatment. In addition, cleaning may be conducted before the heat treatment or after the heat treatment.

In the case of performing the surface treatment with an undiluted or diluted solution of the mold release agent, the following coating method can be employed. Specifically, the solution is sprayed onto the mold substrate by using spray-coating apparatus. Alternatively, in the case of spin-coating, a spin coater is used and the mold substrate is spun after the solution is dropped onto the mold substrate or while the solution is dropped. It is preferable to carry out heat drying at a room temperature to 150° C. after the coating.

In the case of the alkoxysilane compound of formula (1), a solution prepared by dilution with a solvent is effectively and preferably used although an undiluted solution is also used with no problem. Examples of the solvents include the following substances: water, alcohol solvents such as methanol and ethanol; hydrocarbon solvents such as pentane, hexane, cyclohexane, heptane, isooctane, benzene, toluene, and xylene; ketone solvents such as acetone and methyl isobutyl ketone; ether solvents such as diethyl ether, tetrahydrofuran, and dioxane; ester solvents such as ethyl acetate and butyl acetate; aprotic polar solvents such as acetonitrile and N,N-dimethylformamide; and chlorinated hydrocarbon solvents such as dichloromethane and chloroform. In particular, water and alcohol solutions are preferable. As for the concentration of the alkoxysilane compound, a solution prepared by dilution to 0.001 to 50% by weight as the content of the alkoxysilane compound is preferably used.

The treatment can be conducted by spray-coating or spin-coating of the alkoxysilane partially or entirely hydrolyzed in advance or immersing the mold substrate therein. In the spray-coating or spin-coating, it is also effective to make the solvent used for the dilution of the basic component solution or another appropriate solvent be applied on and brought into contact with the substrate in advance in order to improve the fitting of the solution with the substrate.

It is preferred to conduct the heat treatment after the coating. The heat treatment plays an auxiliary role for reaction acceleration and the heating temperature is preferable at 100° C. or more. However, the treatment is not necessarily limited by this condition.

Furthermore, it is preferred to perform cleaning after the heat treatment in order to remove residue, contamination, impurity, etc. on the substrate. For the cleaning, purified water, alcohol, another solvent, or non-etching cleaning agent can be used.

In the case of the silazane compound of formula (2), a solution prepared by dilution with a solvent is effectively and preferably used although an undiluted solution is also used with no problem. Examples of the solvents include the following substances: alcohol solvents such as methanol and ethanol; hydrocarbon solvents such as pentane, hexane, cyclohexane, heptane, isooctane, benzene, toluene, and xylene; ketone solvents such as acetone and methyl isobutyl ketone; ether solvents such as diethyl ether, tetrahydrofuran, and dioxane; ester solvents such as ethyl acetate and butyl acetate; aprotic polar solvents such as acetonitrile and N,N-dimethylformamide; and chlorinated hydrocarbon solvents such as dichloromethane and chloroform. As for the concentration of the silazane compound, a solution prepared by dilution to 0.001 to 50% by weight as the content of the silazane compound is preferably used.

When the mold substrate is treated, immersion treatment, spin-coating, spray-coating, or gas-phase treatment method can be employed. Among them, gas-phase coating is the optimum method in view of prevention of contamination and adherence of an excess substance. In the case of the gas-phase coating, the silazane compound solution is evaporated at an ordinary temperature or by heating and the vapor is brought into contact and reacted with the substrate. Besides the heating, the evaporation by bubbling of a dry nitrogen gas is effectively assisted.

EXAMPLES

Now, the present invention will be described specifically by showing Examples, Comparative Examples, and Reference Examples, but the present invention is not to be restricted the following Examples.

Example 1

For a synthetic quartz glass substrate, processing from lapping to final polishing was performed and then cleaning equivalent to semiconductor cleaning was performed. Fur- thermore, the glass substrate was turned to a hydrophilic substrate by UV-ozone treatment and then immersed in a low-molecular silazane compound having a fluoroalkyl group represented by the following formula (15) for 2 hours. Thereafter, ultrasonic cleaning by ethanol and drying at 110° C. for 30 minutes were conducted. Water (1 µl) or tetradecane (5 µl) was dropped onto the surface-treated glass substrate and the contact angle thereof was measured. For the sliding angle, water (13 µl) was dropped onto the glass. The glass was tilted and the angle when the water droplet begun to move was measured. Furthermore, the difference between the advancing contact angle and the receding contact angle (hysteresis) at this time was calculated. The result is shown in Table 3.

(15)

Example 2

The same treatment as that in Example 1 was performed with use of a low-molecular silazane compound of the following formula (16), and the same evaluation as that in Example 1 was performed. The result is shown in Table 3.

(16)

Example 3

For a synthetic quartz glass substrate, processing from lapping to final polishing was performed and then cleaning equivalent to semiconductor cleaning was performed. After the cleaning, the synthetic quartz glass substrate was heated in a hermetically-sealed container together with the compound of the above-described formula (15). The heating treatment was conducted at 120° C. for 6 hours. After the treatment, the glass substrate was cleaned by an ethanol solution and purified water and then dried. The same evaluation as that in Example 1 was performed. The result is shown in Table 3.

Comparative Example 1

The same treatment as that in Example 1 was performed with the use of a compound of the following formula (17), and the same evaluation as that in Example 1 was performed. The result is shown in Table 3.

(17)

TABLE 3

| | Contact angle (°) | | Sliding angle (°) | |
| --- | --- | --- | --- | --- |
| | Water | Tetradecane | Water | Hysteresis |
| Example 1 | 95 | 41 | 19 | 14 |
| Example 2 | 95 | 42 | 18 | 12 |
| Example 3 | 95 | 41 | 18 | 14 |
| Comparative Example 1 | 92 | 41 | 43 | 26 |

From the above result, the following facts were obtained. Specifically, the silazane compound of the present invention has water repellency and oil repellency equivalent to those of a compound containing many fluorine atoms and has an excellent sliding property because the water droplet begun to slide at a low sliding angle and the hysteresis was also small. Furthermore, as the measurement result of the gas-phase treatment, a result equivalent to that of the case of treatment with a compound undiluted solution was obtained. Thus, it turns out that contamination and adherence of an excess substance can be prevented and therefore the gas-phase treatment is more preferable.

Example 4

First, 0.1 mol of a low-molecular alkoxysilane compound having a fluoroalkyl group represented by the following formula (18) was added to a mixed liquid of 13 g of 0.2 weight % aqueous acetic acid and 44 g of ethanol and this mixture was stirred for 2 hours. In the resulting solution, a soda-lime glass plate was immersed for 2 hours. The soda-lime glass plate was dried at 70° C. for 2 hours after being taken out from the solution. Water (1 µl) or tetradecane (5 µl) was dropped onto the surface-treated glass plate and the contact angle thereof was measured. Furthermore, for the sliding angle, water (13 µl) was dropped onto the glass. The glass was tilted and the angle when the water droplet begun to move was measured. The difference between the advancing contact angle and the receding contact angle (hysteresis) at this time was calculated. The result is shown in Table 4.

(18)

wherein Me denotes a methyl group.

Example 5

For a synthetic quartz glass substrate, processing from lapping to final polishing was performed and then cleaning equivalent to semiconductor cleaning was performed. After the cleaning, the synthetic quartz glass substrate was heated in a hermetically-sealed container together with the compound of the above-described formula (18). The heating treatment was conducted at 74° C. for 6 hours. After the treatment, the glass substrate was cleaned by an ethanol solution and purified water and then dried. The same evaluation as that in Example 4 was performed. The result is shown in Table 4.

Comparative Examples 2 to 4

The same treatment and evaluation were performed with the use of the following fluoroalkylalkoxysilane compounds instead of the alkoxysilane compound of formula (18) in Example 4. The results are shown in Table 4.

The fluoroalkylalkoxysilane compounds used in Comparative Examples 2 to 4 are the following compounds.

Comparative Example 2

8,8,8,7,7,6,6,5,5,4,4,3,3-tetradecafluorooctyl-trimethoxysilane

Comparative Example 3

6,6,6,5,5,4,4,3,3-nonafluorohexyltrimethoxysilane

Comparative Example 4

3,3,3-trifluoropropyltrimethoxysilane

TABLE 4

|  | Contact angle (°) | | Sliding angle (°) | |
| --- | --- | --- | --- | --- |
|  | Water | Tetradecane | Water | Hysteresis |
| Example 4 | 87 | 48 | 18 | 10 |
| Example 5 | 85 | 47 | 12 | 11 |
| Comparative Example 2 | 102 | 53 | 34 | 22 |
| Comparative Example 3 | 96 | 50 | 44 | 23 |
| Comparative Example 4 | 72 | 37 | 29 | 16 |

From the above result, it turns out that the alkoxysilane compound of the present invention has water repellency and oil repellency almost equivalent to those of a fluoroalkyl compound having a longer chain but has a more excellent sliding property. It can be said that it is a lower molecular substance and has a more excellent peel property compared with the known substances.

Reference Example 1

A flask equipped with a stirrer, a reflux condenser, a dropping funnel and a thermometer was charged with 268 g (1.3 mol) of an olefin represented by the following formula (19), (19)

and a toluene solution of a platinum-1,3-divinyl-1,1,3,3-tetramethyldisiloxane complex ($2.0 \times 10^{-4}$ mol based on the olefin), followed by heating to 70° C. After the internal temperature became stable, 123 g (1.3 mol) of dimethylchlorosilane was added dropwise to the flask over five hours at 65 to 75° C., and the reaction mixture was stirred at that temperature for two hours. By distillation, 360 g of a colorless transparent fraction with a boiling point of 96° C./5.0 kPa was obtained, which was confirmed to be a compound of the following formula (20).

(20)

A flask equipped with a stirrer, a reflux condenser, a dropping funnel and a thermometer was charged with 182 g (0.60 mol) of the compound of the above general formula (20) and 300 g of toluene, and ammonia gas was fed thereinto at room temperature over three hours. After the pH of the exhaust gas changed to be basic, a salt was removed by filtration. By distillation of the reaction mixture thus obtained, 140 g of a colorless transparent fraction with a boiling point of 121 to 122° C./0.2 kPa was obtained.

Figure 1:
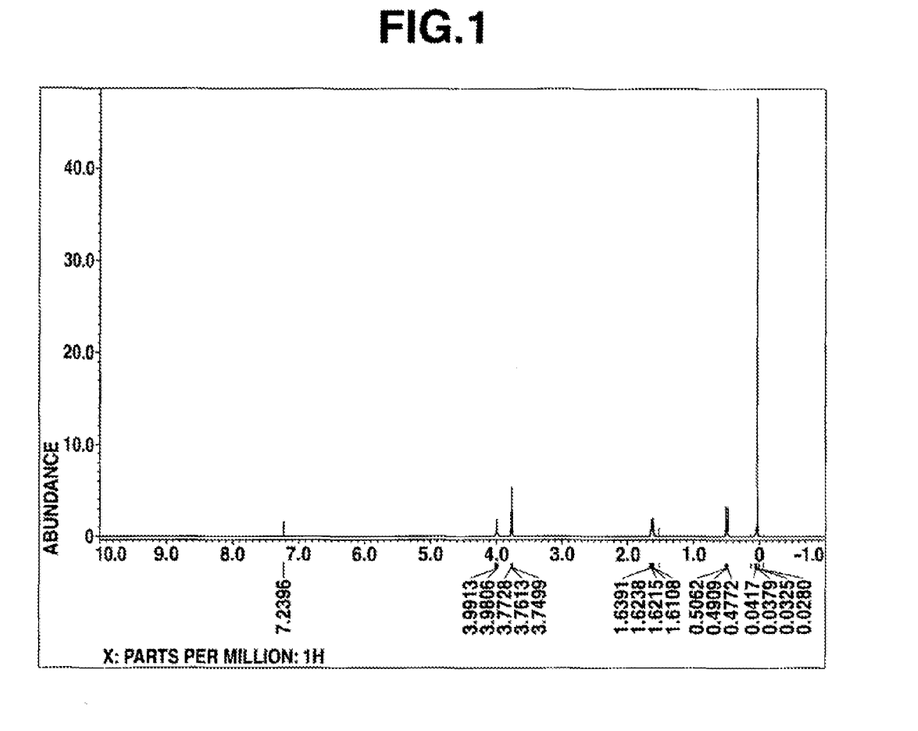
FIG. 1 shows $^1$H-NMR spectrum of a silazane compound obtained in Reference Example 1.
Figure 2:
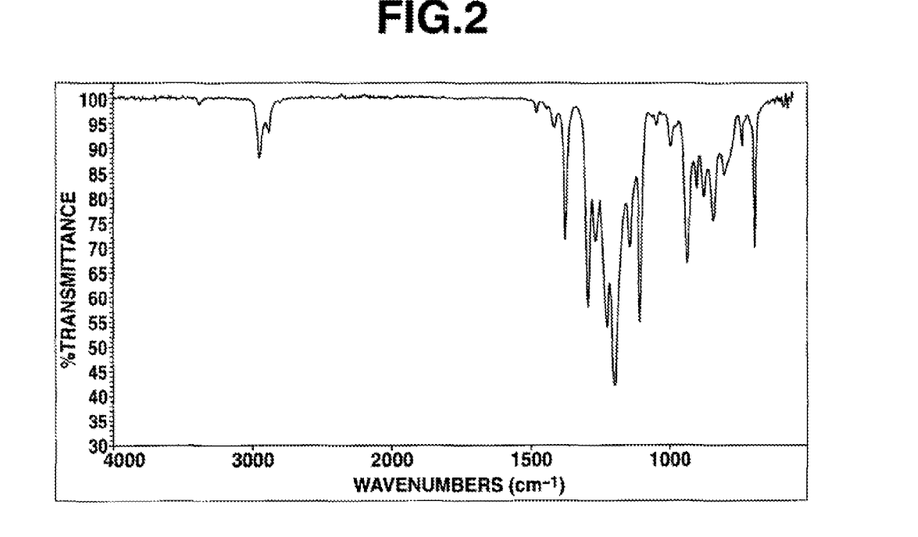
FIG. 2 shows IR spectrum of the silazane compound obtained in Reference Example 1.

The fraction obtained was subjected to measurement of mass spectrum, $^1$H-NMR spectrum (heavy chloroform solvent), and IR spectrum, by a chemical ionization method using isobutane gas as a reaction gas. The result of mass spectrum is set forth below. In addition, FIG. 1 shows a $^1$H-NMR spectrum chart, and FIG. 2 shows an IR spectrum chart.

Mass Spectrum: m/z 550, 398, 267, 202, 142

Based on the above results, the compound obtained was identified as a compound of the following formula (15).

(15)

Reference Example 2

A flask equipped with a stirrer, a reflux condenser, a dropping funnel and a thermometer was charged with 32 g (0.44 mol) of diethylamine and 100 g of toluene. Then, 61 g (0.20 mol) of the compound of the above general formula (20) was added dropwise to the flask over three hours under water cooling, and the mixture in the flask was stirred for three hours at room temperature. After a salt was removed by filtration, the resulting reaction mixture was distilled, to obtain 57 g of a colorless transparent fraction with a boiling point of 97 to 98° C./2.0 kPa.

Figure 3:
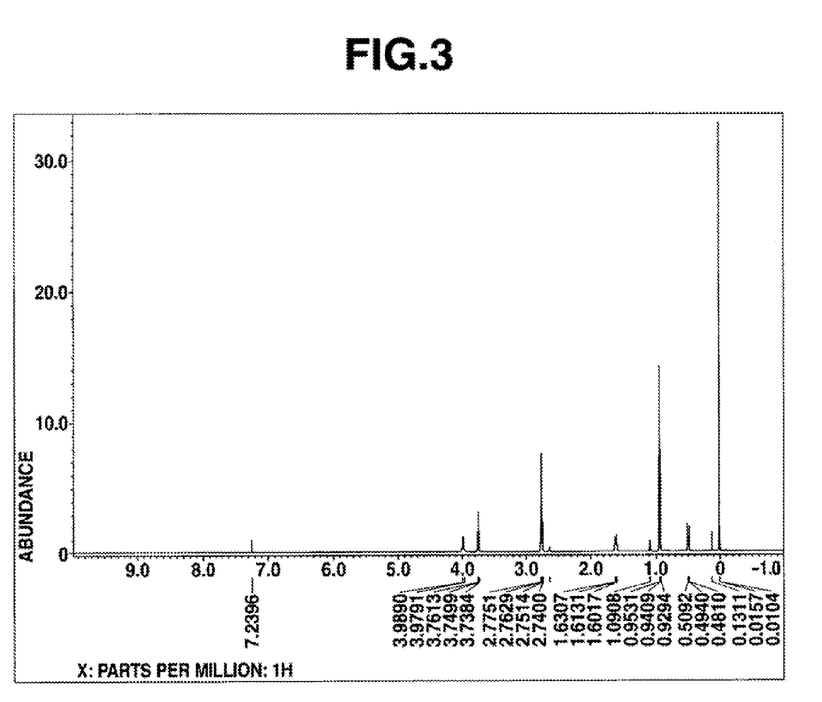
FIG. 3 shows $^1$H-NMR spectrum of a silazane compound obtained in Reference Example 2.
Figure 4:
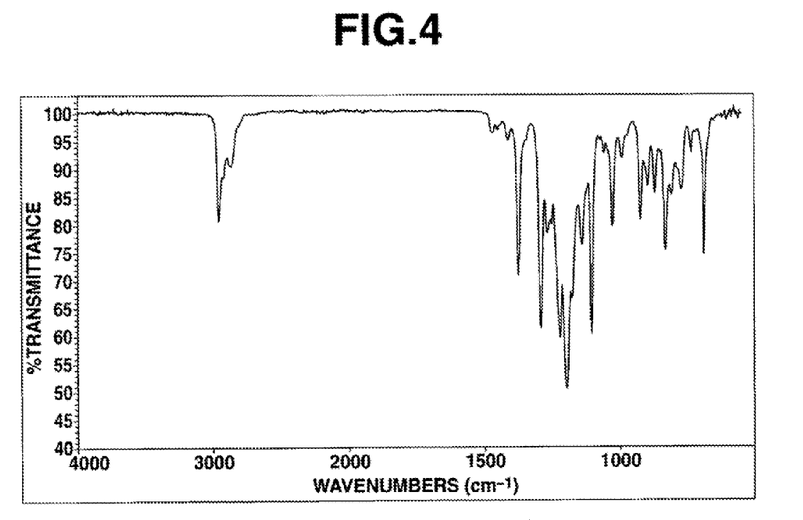
FIG. 4 shows IR spectrum of the silazane compound obtained in Reference Example 2.

The fraction thus obtained was subjected to measurement of mass spectrum, $^1$H-NMR spectrum (heavy chloroform solvent), and IR spectrum. The result of mass spectrum is set forth below. In addition, FIG. 3 shows a $^1$H-NMR spectrum chart, and FIG. 4 shows an IR spectrum chart.

Mass Spectrum: m/z 339, 324, 267, 225, 130

Based on the above results, the compound obtained was identified as a compound of the following formula (16).

(16)

Reference Example 3

A flask equipped with a stirrer, a reflux condenser, a dropping funnel and a thermometer was charged with 31 g (0.15 mol) of an olefin represented by the above formula (19), and a toluene solution of a platinum-1,3-divinyl-1,1,3,3-tetramethyldisiloxane complex ($1.0\times10^{-4}$ mol based on the olefin), followed by heating to 70° C. After the internal temperature became stable, 19 g (0.14 mol) of trichlorosilane was added dropwise to the flask over four hours at 70 to 80° C., and the reaction mixture was stirred at that temperature for two hours. It was confirmed to be a compound of the following formula (21).

(21)

After cooling to a room temperature, 47 g (0.46 mol) of triethylamine and 125 ml of toluene were placed. Then, 15 g (0.46 mol) of methanol was dropped at 20 to 30° C. over 2 hours and the mixture was stirred at this temperature for 1 hour. Thereafter, water was added to dissolve the generated-triethylamine hydrochloride, followed by liquid-liquid extraction. Then, the organic layer was distilled to obtain 35 g of a clear, colorless fraction with a boiling point of 111 to 112° C./5.0 kPa.

Figure 5:
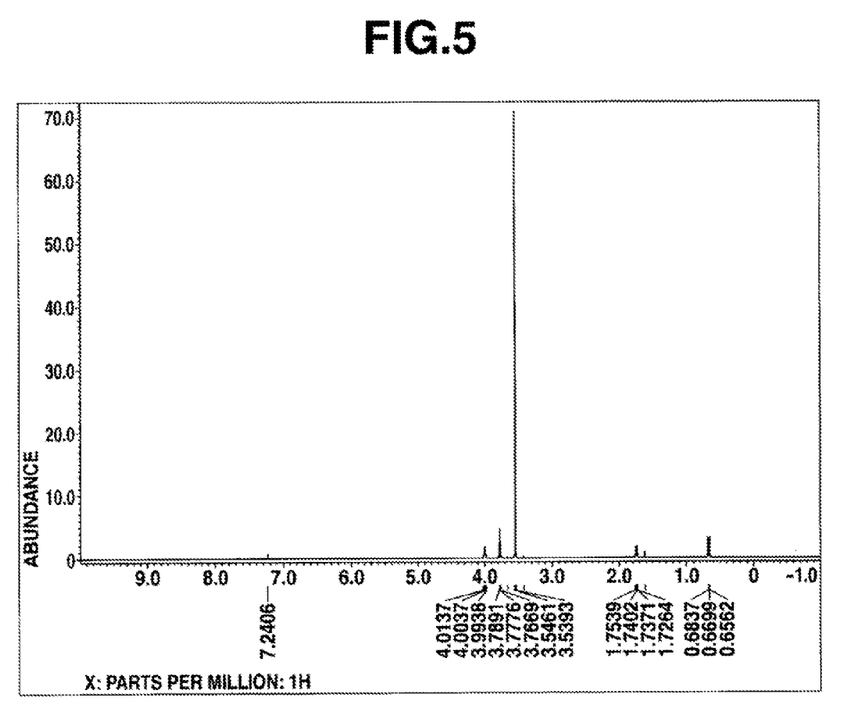
FIG. 5 shows $^1$H-NMR spectrum of an alkoxysilane compound obtained in Reference Example 3.
Figure 6:
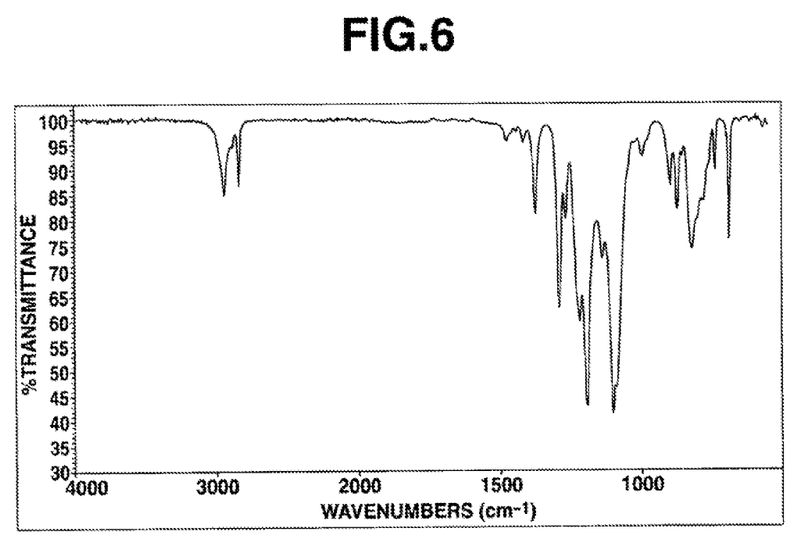
FIG. 6 shows IR spectrum of the alkoxysilane compound obtained in Reference Example 3.

The fraction obtained was subjected to measurement of mass spectrum, $^1$H-NMR spectrum (heavy chloroform solvent), and IR spectrum, by a chemical ionization method using isobutane gas as a reaction gas. The result of mass spectrum is set forth below. In addition, FIG. 5 shows a $^1$H-NMR spectrum chart, and FIG. 6 shows an IR spectrum chart.

Mass Spectrum: m/z 331, 299, 257, 163, 121

Based on the above results, the compound obtained was identified as a compound of the following formula (18).

(18)

wherein Me denotes a methyl group.

Japanese Patent Application No. 2011-087896 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A nanoimprint-mold release agent comprising an alkoxysilane compound represented by the following general formula (1) or a silazane compound represented by the following general formula (2):

(1)

wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^2$ and $R^3$ are each independently methyl group or ethyl group; X and Y are each independently an ether linkage or an ester linkage; a and b are each 0 or 1; m, n, and p are each an integer of 0 to 6; q is an integer of 1 to 6 and r is an integer of 0 to 2, (2)

wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^4$ and $R^5$ are each independently an aliphatic monovalent hydrocarbon group of 1 to 6 carbon atoms in which a part or all of hydrogen atoms bonded to carbon atoms may be substituted; $R^6$ is a hydrogen atom or an aliphatic monovalent hydrocarbon group of 1 to 6 carbon atoms in which a part or all of hydrogen atoms bonded to carbon atoms may be substituted; a and b are each 0 or 1; m, n, and p are each an integer of 0 to 6; q is an integer of 1 to 6 and s is 1 or 2.

2. The mold release agent according to claim 1, wherein the alkoxysilane compound of formula (1) is an alkoxysilane compound represented by the following general formula (3), (4), or (5):

(3)

wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^2$ and $R^3$ are each independently methyl group or ethyl group; X is an ether linkage or an ester linkage; q is an integer of 1 to 6 and r is an integer of 0 to 2, (4)

wherein $R_f$ and $R_f'$ are each independently a fluoroalkyl group of 1 to 10 carbon atoms; $R^1$ is a hydrogen atom or an aliphatic monovalent hydrocarbon group of 1 to 6 carbon atoms; $R^2$ and $R^3$ are each independently methyl group or ethyl group; X and Y are each independently an ether linkage or an ester linkage; q is an integer of 1 to 6 and r is an integer of 0 to 2, (5)

wherein $R_f$ and $R_f'$ are each independently a fluoroalkyl group of 1 to 10 carbon atoms; $R^{1'}$ is a hydrogen atom or an aliphatic monovalent hydrocarbon group of 1 to 6 carbon atoms; $R^2$ and $R^3$ are each independently methyl group or ethyl group; q is an integer of 1 to 6 and r is an integer of 0 to 2.

3. The mold release agent according to claim 1, wherein the silazane compound of formula (2) is a silazane compound represented by the following general formula (10), (11), or (12):

(10)

wherein $R_f$ and $R_f'$ are each independently a fluoroalkyl group of 1 to 10 carbon atoms; $R^{1'}$ is a hydrogen atom or an aliphatic monovalent hydrocarbon group of 1 to 6 carbon atoms; $R^4$ and $R^5$ are each independently an aliphatic monovalent hydrocarbon group of 1 to 6 carbon atoms in which a part or all of hydrogen atoms bonded to carbon atoms may be substituted; $R^6$ is a hydrogen atom or an aliphatic monovalent hydrocarbon group of 1 to 6 carbon atoms in which a part or all of hydrogen atoms bonded to carbon atoms may be substituted; q is an integer of 1 to 6 and s is 1 or 2, (11)

wherein $R_f$ and $R_f'$ are each independently a fluoroalkyl group of 1 to 10 carbon atoms; $R^{1'}$ is a hydrogen atom or an aliphatic monovalent hydrocarbon group of 1 to 6 carbon atoms; $R^4$ and $R^5$ are each independently an aliphatic monovalent hydrocarbon group of 1 to 6 carbon atoms in which a part or all of hydrogen atoms bonded to carbon atoms may be substituted; $R^6$ is a hydrogen atom or an aliphatic monovalent hydrocarbon group of 1 to 6 carbon atoms in which a part or all of hydrogen atoms bonded to carbon atoms may be substituted; q is an integer of 1 to 6 and s is 1 or 2, (12)

wherein $R_f$ and $R_f'$ are each independently a fluoroalkyl group of 1 to 10 carbon atoms; $R^{1'}$ is a hydrogen atom or an aliphatic monovalent hydrocarbon group of 1 to 6 carbon atoms; $R^4$ and $R^5$ are each independently an aliphatic monovalent hydrocarbon group of 1 to 6 carbon atoms in which a part or all of hydrogen atoms bonded to carbon atoms may be substituted; $R^6$ is a hydrogen atom or an aliphatic monovalent hydrocarbon group of 1 to 6 carbon atoms in which a part or all of hydrogen atoms bonded to carbon atoms may be substituted; q is an integer of 1 to 6 and s is 1 or 2.

4. A method of surface treating a nanoimprint-mold comprising treating the surface of a nanoimprint mold by the nanoimprint-mold release agent according to any one of claims 1 to 3.

5. The method according to claim 4, wherein the surface treatment method is any of gas-phase treatment, immersion treatment, and coating treatment.

6. A nanoimprint mold obtained by the surface treatment method according to claim 4.

* * * * *